United States Patent [19]

Steer

[11] Patent Number: 4,867,749

[45] Date of Patent: Sep. 19, 1989

[54] UROSTOMY APPLIANCE

[75] Inventor: Peter L. Steer, Surrey, England

[73] Assignee: E.R. Squibb and Sons, Inc., Princeton, N.J.

[21] Appl. No.: 804,010

[22] Filed: Nov. 20, 1985

[30] Foreign Application Priority Data

Mar. 15, 1985 [GB] United Kingdom ................ 8506733

[51] Int. Cl.⁴ ............................................. A61F 5/44
[52] U.S. Cl. ................................................. 604/337
[58] Field of Search ................................ 604/332–345

[56] References Cited

U.S. PATENT DOCUMENTS

| 2,528,227 | 10/1950 | Johnson | 604/343 |
| 3,557,790 | 1/1971 | Hauser | 604/342 |
| 4,170,231 | 10/1979 | Collins | 604/333 |
| 4,460,363 | 7/1984 | Steer et al. | 604/336 |
| 4,477,325 | 10/1984 | Osburn | 604/336 |

FOREIGN PATENT DOCUMENTS

| 3218092 | 11/1983 | Fed. Rep. of Germany | 604/332 |
| 217480 | 6/1924 | United Kingdom . | |
| 555852 | 10/1943 | United Kingdom . | |
| 663253 | 12/1951 | United Kingdom . | |
| 696954 | 9/1953 | United Kingdom . | |
| 1217406 | 12/1970 | United Kingdom . | |
| 1217406 | 12/1970 | United Kingdom . | |
| 1455784 | 11/1976 | United Kingdom | 604/337 |
| 1470419 | 4/1977 | United Kingdom . | |

Primary Examiner—Jerome L. Kruter
Attorney, Agent, or Firm—Donald J. Barrack; Robert E. Lee, Jr.

[57] ABSTRACT

A urostomy appliance has one part which is attachable to the body of the wearer by a pad of medical grade adhesive. The pad has a central hole, and, on its side remote from the skin of the wearer, a coupling element. The first part above mentioned is constructed to cooperate with a second part consisting of a single piece of moulded plastics material. The second part includes a coupling element constructed for a snap fit or a push fit engagement with the first coupling element. Moreover, it has a cover wall in the shape of a dome and an outlet pipe.

5 Claims, 2 Drawing Sheets

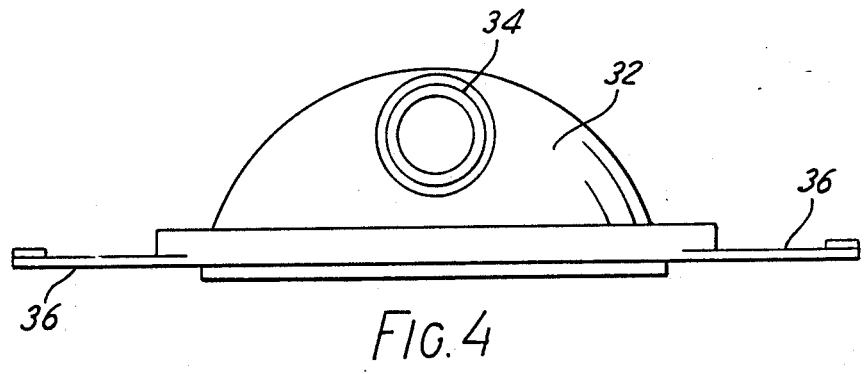
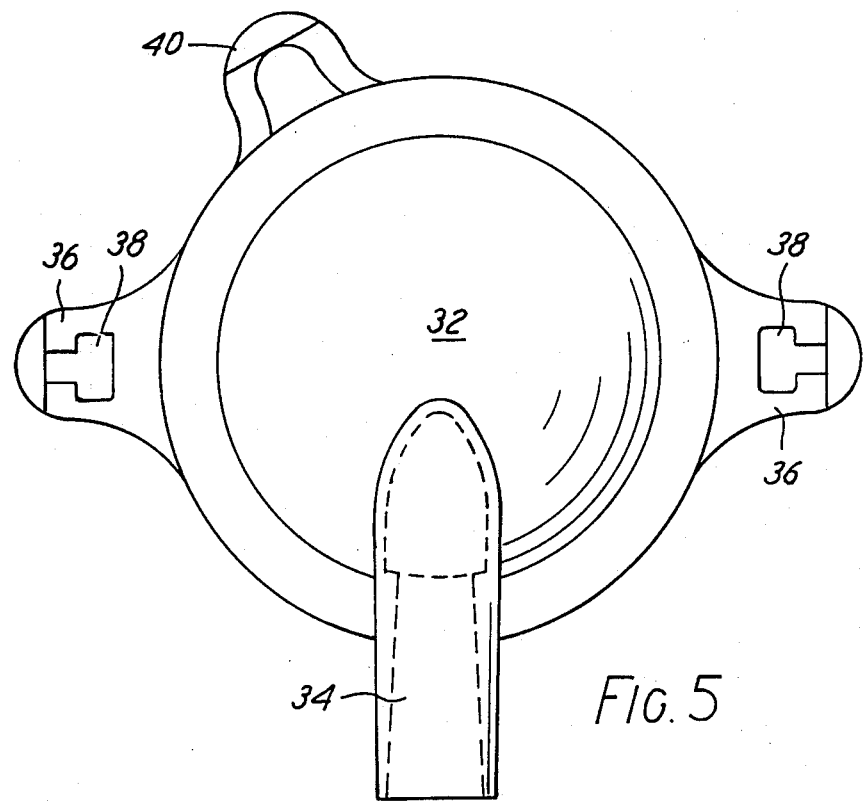

UROSTOMY APPLIANCE

BACKGROUND OF THE INVENTION

The invention relates to a urostomy appliance.

There have been numerous attempts in the past to provide a urostomy appliance which is comfortable to wear, unobtrusive, leakproof in all normal circumstances, and easy to attach and detach. Other desirable features of such an appliance are that it should be easy and inexpensive to manufacture, and when attached in the normal wearing position, should be securely attached. This is important so that the wearer can have confidence in the device and live near to a normal life.

Prior attempts which are to be found in the patent literature include the following.

British Patent No. 217 480 of Franklin discloses a drainage apparatus made of rubber which is intended to be attached by a belt. It has a collection chamber and downwardly extending outlet pipe. This early design, it is believed, would not be easy to attach and detach, might leak, and would not give a feeling of security.

Paterson in British Patent No. 663 253 discloses an appliance for collecting uncontrolled excretions which has a domed wall and an outlet pipe; there is a sheet of soft pliable rubber held to the body by an arrangement of belts. This device, it is believed, would suffer from the disadvantages discussed above.

In British Patent No. 696,954, FIG. 8, Berg discloses a surgical appliance having a dome shaped collection vessel and an outlet pipe, intended for an excrement of fluid nature. A moulded rubber ring is held in contact with the body by a belt and harness stucture.

In British Patent No. 1,404,959, Sherwood Medical Industries Inc. disclose a wound drainage apparatus permitting one to use suction for draining a wound. This device is strapped to a patient and is evidently intended for use by medically qualified personnel.

It is suggested in British Patent No. 1,470,419 that excreted urine, after urostomy surgery, could be collected in a drainage bag applied at the zone of the surgery. U.S. Pat. No. 1,470,419 is directed to adhesive means for securing such a bag. In accordance with the present invention, it is believed that it will be preferable for a person suffering from a urostomy to be able to attach a urine collection bag at a remote distance from the place of surgery. This is likely to be particularly important for sleeping, as it enables a night drainage bag to be connected.

In U.S. Pat. No. 2,528,227 of Johnson there is a disclosure of an ileostomy bottle, but this is intended to be attached to the wearer by a double belt arrangement; it is believed that this device would be cumbersome, obtrusive and not easily attached and removed.

There remains a need for a compact, effective and unobtrusive urostomy appliance.

SUMMARY OF THE INVENTION

According to the present invention, there is provided a urostomy appliance comprising one part which is attachable to the body of the wearer by a pad of medical grade adhesive, the pad having a central hole and, on its side remote from the skin of the wearer, a coupling element, this part being constructed to co-operate with a second part consisting of a single piece of moulded plastics material, the second part including a coupling element constructed for a snap fit or push fit engagement with the first coupling element, a cover wall which is preferably in the shape of a shallow dome, and an outlet pipe.

Optionally the second part may have integral ears to which a belt may be attached, and/or an integral tab which the user can grip and pull to separate the two parts.

Further novel and advantageous features of the present invention will be understood from the following description of an illustrative embodiment thereof, given with reference to the accompanying drawings in which:

BRIEF DESCRIPTION OF THE DRAWINGS

FIG. 4 is an underplan view of the second part shown in FIG. 3;

FIG. 5 is a front elevation of the second part shown in FIGS. 2-4; and

In the following description and throughout the drawings, like parts are given like reference numerals.

DETAILED DESCRIPTION OF THE DRAWINGS

Figure 1:
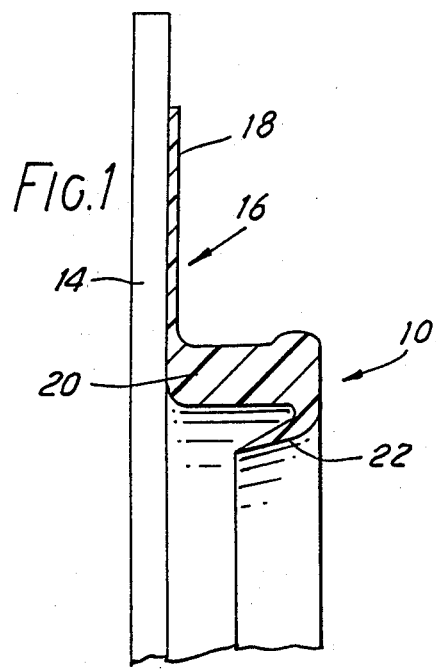
FIG. 1 is a vertical central cross-section through a first part of one example of a urostomy appliance according to the present invention.
Figure 6:
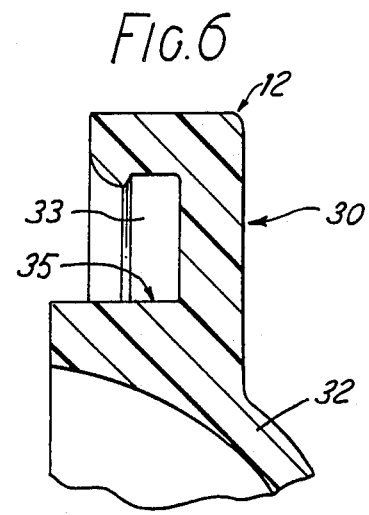
FIG. 6 is a detail view in cross-section snowing one example of a suitable form of coupling element on the second part.
Figure 2:
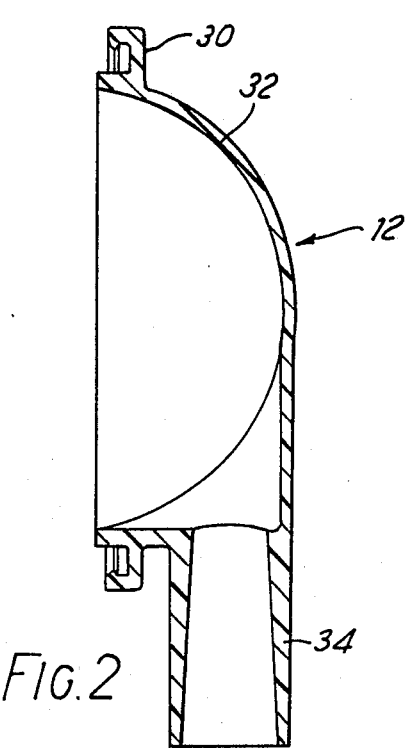
FIG. 2 is a similar vertical cross-sectional view through a second part intended for co-operation with the first part of FIG. 1.
Figure 3:
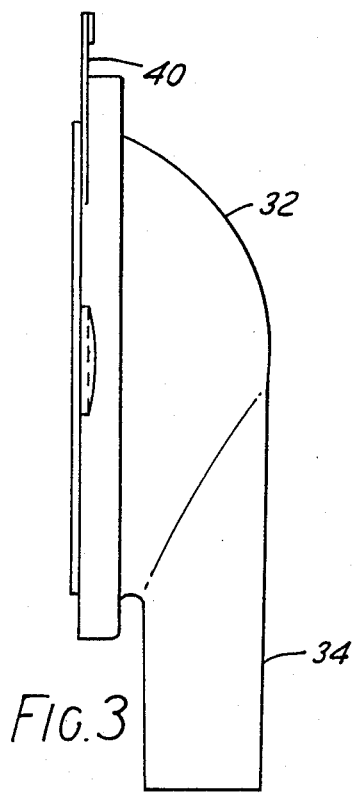
FIG. 3 is a side view of the second part or the urostomy appliance shown in FIG. 2.

Referring firstly to FIGS. 1,2 and 6, the illustrated urostomy appliance has a first part 10 and a second part 12. The first part 10 includes a pad 14 of medical grade adhesive material, to which is attached a first coupling element 16. The coupling element 16 has a laterally extending flange 18, an annular wall 20, and an inwardly directed flexible sealing skirt 22. In use, this skirt engages the wall indicated at 35 in FIG. 6.

Suitable medical grade adhesive materials, which may be used for pad 14, comprise pressure sensitive adhesive formulations that consist of a homogeneous blend of one or more water soluble or water swellable hydrocolloids dispersed in a viscous elastomeric substance such as polyisobutylene as disclosed by Chen in U.S. Pat. No. 3,339,506. Optionally, the adhesive composition can also include one or more cohesive strengthening agents described by Chen et al. in U.S. Pat. No. 4,192,785 or one or more hydratable natural or synthetic polymers as described by Pawelchak et al. in U.S. Pat. No. 4,393,080. Other medical grade adhesives designed for ostomates and available on the market are also suitable.

The second part 12 includes a second coupling element 30, a dome wall 32, and an outlet pipe 34. The second part is preferably moulded in one piece from a synthetic plastics material, such as that known as ethylene vinyl acetate 502. Optionally there may also be moulded therewith a pair of ears 36 having apertures 38 for attachment of a lightweight belt or elastic strap and tab 40 positoned so that it can be gripped by the wearer of the device when it is desired to separate the two coupling elements and so remove the second part 12 from the first part 10. In many applications, however, the ears 36 and belt may be omitted and the device may be quite satisfactorily held on merely by the adhesion of the pad 14 to the skin of the wearer.

In use, the person who is to wear the urostomy appliance cuts a hole of appropriate diameter in the pad 14, within the periphery defined by the wall 20 of the first coupling element. Conventional measures such as having a small central hole in the pad and slitting, or showing outlines of circles on the packaging, may be employed to assist the cutting of this hole. It is intended for reception of the stoma. The wearer then applies the pad of the first part 10 to his body, whereupon he is ready to effect, by a push fit or a snap fit, temporary but secure joining of the first and second coupling elements. As is seen from FIGS. 1 and 6, the annular wall portion 20 bearing the flexible seal strip 22 is entered into the recess 33 of the second coupling element, leading to a secure attachment which is substantially leakproof between the first part and second part of the urostomy appliance. The space defined by the substantially dome-shaped cover 32 allows space for any projecting portion of the stoma, so it is not irritated, nor is the wearer pained by rubbing or abrasion. Any discharged urine can exit via the pipe 34. Of course it will be understood that a drainage tube is attached to the outlet pipe 34. If desired, but this is not essential, the drainage tube may be connected to the outlet pipe 34 by forming these two parts according to the teaching of European Pat. No. 57057 or its British equivalent Patent No. 2,062,690.

It will be seen that the urostomy appliance particularly disclosed and illustrated herein is compact, unobtrusive, leakproof in all normal circumstances, and easy to attach and detach. Moreover the use of the medical grade adhesive pad 14 renders it securely attached to the body.

I claim:

1. A two piece urostomy appliance comprising:
  (a) a first part which is attachable to the body of the wearer by a pad of medical grade adhesive, the pad having a central hole and, on its side remote from the skin of the wearer, a first coupling element, said first part being constructed to cooperate with a second part consisting of a single piece of molded plastic material;
  (b) a second part including a coupling element constructed for a snap fit or push fit engagement with said first coupling element, a cover wall shaped like a shallow dome, and an outlet pipe.
2. An appliance according to claim 1 in which the second part has ears constructed so that a belt can be attached to them.
3. An appliance according to claim 2 in which the second part has an integral pull tab.
4. An appliance according to claim 1 in which the cover wall is of ethylene vinyl acetate.
5. An appliance according to claim 1 in which said first coupling element has an annular wall and an inwardly-directed flexible skirt.